United States Patent [19]

Kanno et al.

[11] Patent Number: 4,704,520

[45] Date of Patent: Nov. 3, 1987

[54] LIGHT SOURCE DEVICE FOR AN ENDOSCOPE

[75] Inventors: Masahide Kanno; Atsushi Amano, both of Hachioji; Seiichi Hosoda, Fuchu; Shinichiro Hattori, Hachioji, all of Japan

[73] Assignee: Olympus Optical Co., Ltd., Tokyo, Japan

[21] Appl. No.: 729,574

[22] Filed: May 2, 1985

[30] Foreign Application Priority Data

May 2, 1984 [JP] Japan .................. 59-88614

[51] Int. Cl.⁴ .......................... G01J 1/32; A61B 1/06
[52] U.S. Cl. .......................... 250/205; 128/6
[58] Field of Search ............... 250/205; 354/62, 413, 354/416, 417; 128/6, 396–398, 4, 5; 354/420, 422, 423; 362/32, 321, 804

[56] References Cited

U.S. PATENT DOCUMENTS

| 4,048,493 | 9/1977 | Lee ........................ 250/205 |
| 4,356,534 | 10/1982 | Hattori ..................... 362/32 |
| 4,366,529 | 12/1982 | Takahashi et al. ......... 128/6 |
| 4,369,767 | 1/1983 | Shishido ................... 354/62 |
| 4,429,686 | 2/1984 | Hosoda ...................... 128/6 |
| 4,487,489 | 12/1984 | Takamatsu ................. 354/62 |

FOREIGN PATENT DOCUMENTS

| 0027263 | 4/1981 | European Pat. Off. . |
| 2912779 | 10/1979 | Fed. Rep. of Germany . |
| 3323365 | 3/1984 | Fed. Rep. of Germany . |
| 3337454 | 4/1984 | Fed. Rep. of Germany . |
| 2130092 | 5/1984 | United Kingdom . |

Primary Examiner—Edward P. Westin
Assistant Examiner—Charles Wieland

[57] ABSTRACT

Disclosed is a light source device for an endoscope including a lamp to flash or to normally emit light according to current fed thereto, a shutter for photographing, and a diaphragm for photographing/observing. In the light source device, the amount of light emitted is variable. In response to a supplied check start command signal, except when the endoscope body is used, the light source device successively checks at least two of the following items; the operation of the shutter, the operation of the diaphragm, normal light emission of the lamp and the flashing of the lamp. Then, the light source device automatically checks, according to the amount of light detected by a photosensitive element, whether the above functions are operating normally or not, and displays the result of the check.

12 Claims, 5 Drawing Figures

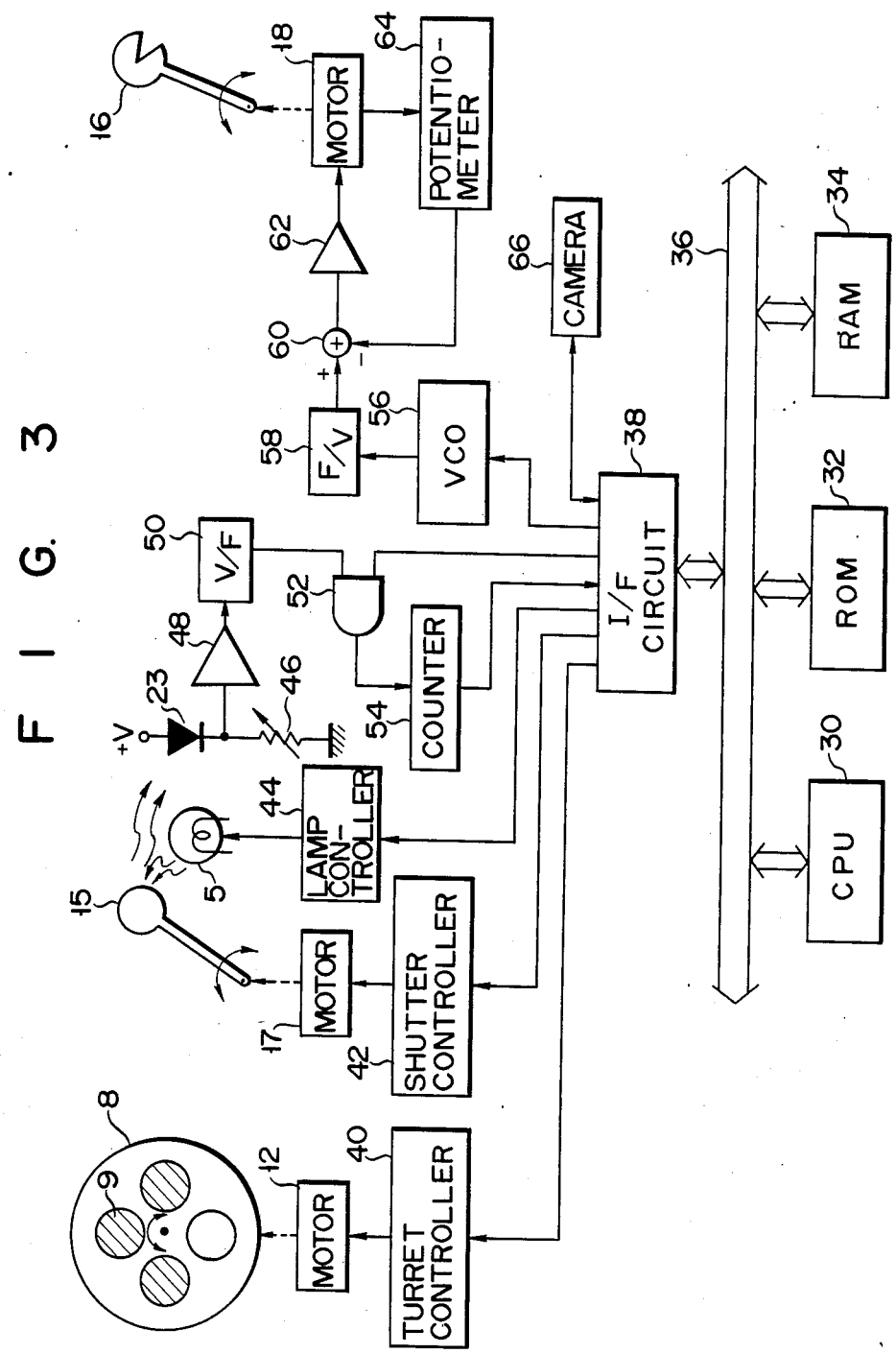

TO STEP 160 (FIG. 4B)

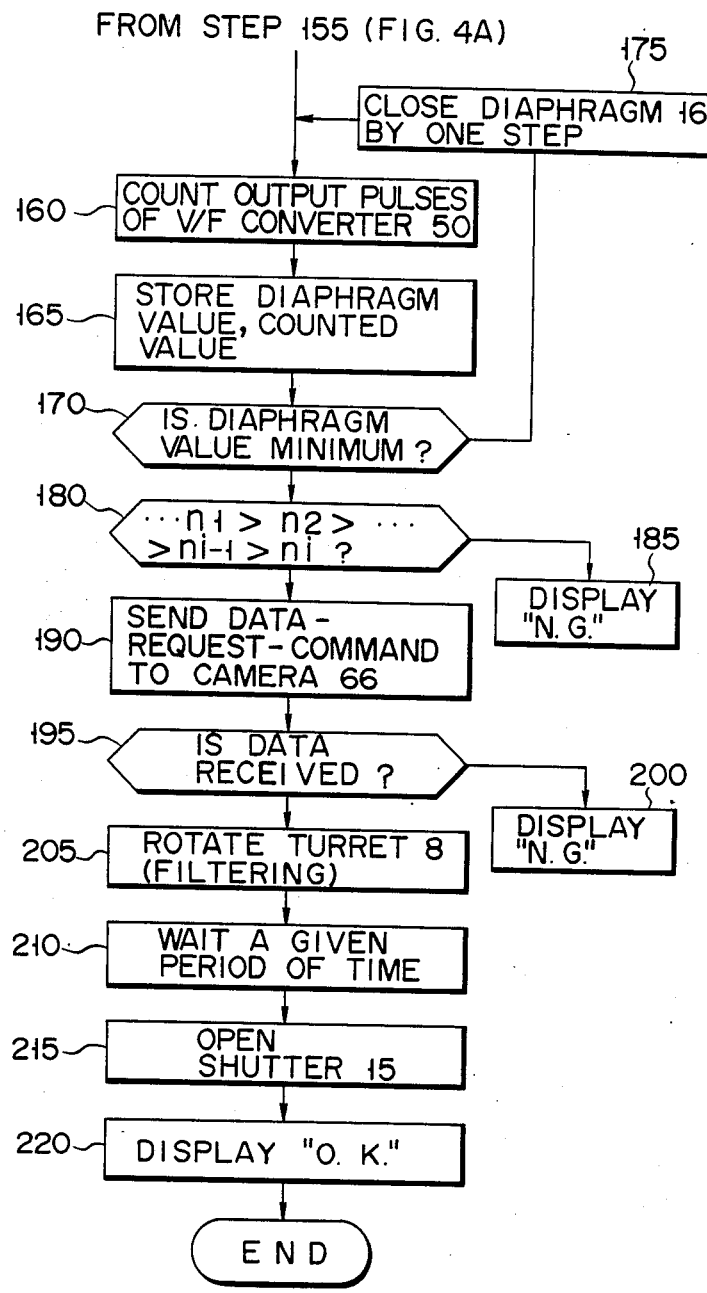

LIGHT SOURCE DEVICE FOR AN ENDOSCOPE

BACKGROUND OF THE INVENTION

The present invention relates to a light source device for an endoscope and, more particularly, to a light source device capable of automatically or manually adjusting an amount of light emitted from the light source device.

An object to be observed by an endoscope is generally the inside of a body cavity or a narrow tubular member. A light source device for illuminating the object is necessarily provided when using the endoscope. The light source device is designed so that the amount of its light is adjustable. The optimum amount of light for illuminating an object, so that it can be properly observed, depends on the distance from the light source device to the object. For diagnosing the body cavity by means of the endoscope, it is frequently required to take a photograph inside the coelom, which of cource is completely dark. In the endoscope photographing system, therefore, the amount of illuminating light from the light source device is varied for adjusting an exposure. This also needs the function of varying the amount of the light from the light source device. The light amount necessary for photographing a target portion is different from that for observing the target portion by the naked eye. This reason additionally requires the function of varying the amount of light from the light source device. The conventional ways to vary the light amount are, for example, to switch lamps from a lamp emitting a small amount of light to that emitting a large amount of light and vice versa, to control a current fed to a lamp, or to control a diaphragm between a lamp and an endoscope.

In the conventional light source device, it can not be known whether the light amount adjusting function of the light source device is normal or not until the light source device is actually operated. An operator may mistakenly apply to an object an endoscope which cannot adjust the light amount correctly. The result is many unavoidable problems. For example, in using medical endoscopes, there is often a case that an abnormality of the light amount adjusting function is found, after an endoscope body is inserted into the body cavity. In this case, it must be pulled out of the body cavity, repaired, and then inserted again into the body cavity. Multiple insertions of the endoscope inflicts pain on a patient which would otherwise not be caused. When photographing inside the coelom, it can be checked if the light amount adjustment functions normally after the film is developed. If it functions abnormally, the photographing must be made again. The result is an unsmooth diagnosis.

SUMMARY OF THE INVENTION

Accordingly, an object of the present invention is to provide a light source device for an endoscope which can check if various functions of the light source device normally operate before the light source device operates.

To achieve the above object, there is provided a light source device for an endoscope comprising a light source with light amount adjusting means and means for checking if the light amount adjusting means normally functions by operating the light amount adjusting means in response to a check start signal.

BRIEF DESCRIPTION OF THE DRAWINGS

FIG. 3 is a block diagram of a control circuit used in this embodiment; and

FIGS. 4A and 4B cooperatively show a flowchart showing the operation of this embodiment.

DETAILED DESCRIPTION OF THE PREFERRED EMBODIMENT

Figure 1:
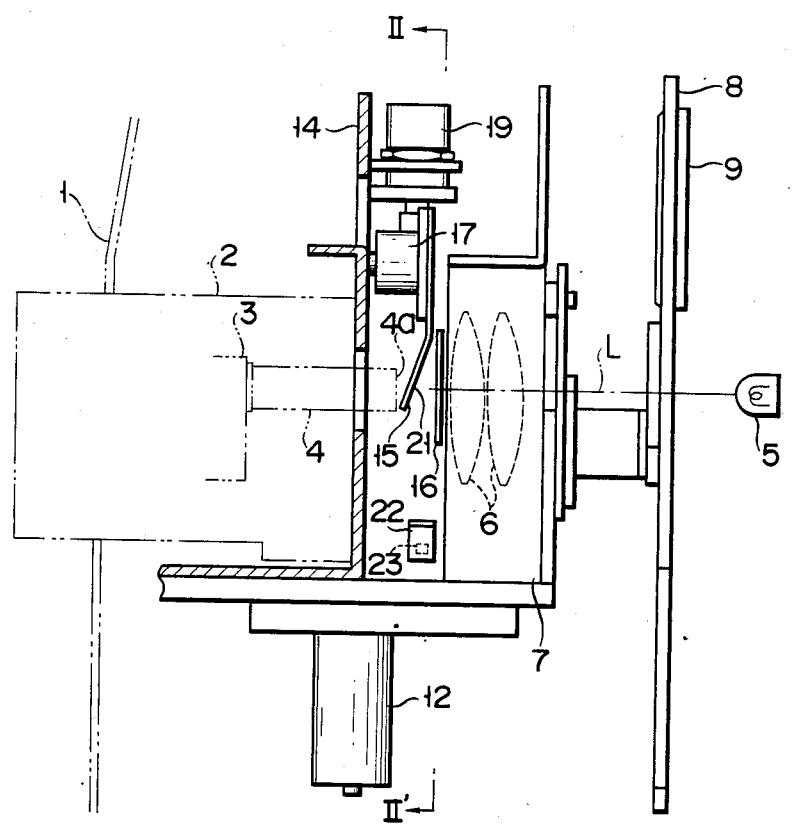
FIG. 1 shows a cross sectional view of a key portion of an embodiment of a light source device for an endoscope according to the present invention.
Figure 2:
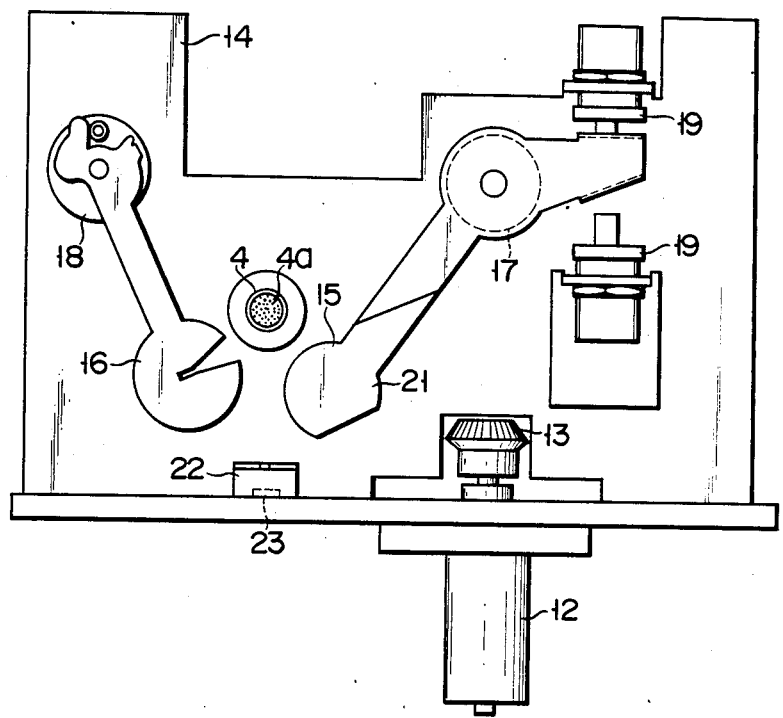
FIG. 2 shows a cross sectional view taken along line II—II' in FIG. 1.

An embodiment of a light source device for an endoscope according to the present invention will be described referring to the accompanying drawings. FIG. 1 illustrates a key portion of a structural arrangement of the embodiment of this invention. FIG. 2 shows a cross sectional view taken along line II—II' in FIG. 1. The light source device for the endoscope may be contained at the distal or far end of an endoscope, which in this embodiment is an external light source device connected to a light guide. As shown, a front panel 1 is provided with a socket 2. A connector 3 provided at an end of the extended part of a light guide code of an endoscope body (not shown) is removably connected to this socket 2. The front panel 1 is also provided with a display section for visually providing the check results. A light guide tube 4 coupled with the connector 3 lies on an optical axis L of a lamp 5 as a light source. Rays of light condensed by a condenser 6 are incident on an incident end surface 4a of the light guide tube 4. The condenser 6 is supported by a lens supporting frame 7. Provided between the the lamp 5 and the condenser 5 is a turret 8 having at its peripheral portion a plurality of color filters 9 with different color characteristics (transmission characteristics) and a mere window (through hole). The turret 8 is rotated by a drive motor 12 so that either of the color filters 9 or the window is selectively positioned on the optical axis L of the lamp 5. For transmitting a rotating force from the drive motor 12 to the turret 8, a gear mechanism such as a bevel gear 13 is used.

Provided on the supporting plate 14 are a shutter vane 15 and a diaphragm vane 16, which are disposed perpendicular to the optical axis L. The shutter vane 15 is used for the shutter operation for photographing. The diaphragm vane 16 is for adjusting a light amount. The shutter vane 15 and the diaphragm vane 16 are respectively driven by motors 17 and 18. In photographing an object, the shutter vane 15 selectively and intermittently interrupts the optical axis of the lamp 5 to effect the shutter operation. The turning range of the shutter vane 15 is limited at both ends by dumpers 19.

The diaphragm vane 16 is cut so that the degree to which the optical axis L of the lamp is interrupted, changes as the diaphragm vane 16 turns. As shown in FIG. 1, the diaphragm vane 16 is located closer to the lamp 5 than the shutter vane 15.

Accordingly, the shutter vane 15 shuts off the light modified by the diaphragm vane 16. A part 21 of the shutter vane 15, positioned on the optical axis L of the lamp 5, is processed as a reflecting surface. Further, the reflecting surface 21 is bent toward the end face 4a of the light guide 4 to have an angle with respect to the optical axis L. With such an angle, the light incident on the shutter vane 15 through the condenser 6 is directed 90° downwardly. The reflecting surface 21, diffuses the light incident thereon. The diffused light from the reflecting surface 21 is incident on a photosensitive element 23. The photosensitive element 23 is set in a shield box 22 for avoiding any unnecessary incident of light. The shield box 22 has a through hole 24. Only the light passed through the through hole 24 is applied to the photosensitive element 23.

FIG. 3 shows a control circuit for controlling the whole light source device under discussion. As shown, a CPU 30, a ROM 32, a RAM 34 and an interface (I/F) circuit 38 are interconnected through a system bus 36. The motor 12 for driving the turret 8 is connected to the I/F circuit 38, through a turret controller 40. The I/F circuit 38 is also connected to the motor 17 for driving the shutter vane 15, through the shutter controller 42. The lamp 5 is controlled by the I/F circuit 38 through a lamp controller 44. A photodiode as the photosensitive element 23 is connected at the anode to a power source +V and at the cathode to ground through a resistor 46. A node between the photosensitive element 23 and the resistor 46 is connected to the first input terminal of an AND gate 52 through an amplifier circuit 48 and a voltage/frequency (V/F) converter 50. The second input terminal of the AND gate 52 is supplied with a signal derived from the I/F circuit 38. The output signal from the AND gate 52 is supplied to a counter 54 of which the output signal is supplied to the I/F circuit 38. The output signal from the I/F circuit 38 is inputted to a variable frequency oscillator (VCO) 56 of which the output signal is supplied to the first input terminal (+) of a mixer 60 through a frequency/voltage (F/V) converter 58. The output signal of the mixer 60 is supplied as a drive signal to the motor 18 for driving the diaphragm vane 16, through an amplifier circuit 62. The amount of turn of the motor 18 is detected in the form of a voltage signal by a potentiometer 64, and is negatively fed back to the second input terminal (−) of the mixer 60. A camera 66, coupled with an eyepiece portion of an endoscope, is also connected to the I/F circuit 38. In this embodiment, data on alphanumeric characters, for example, to be printed on a film, is often transferred between the light source and the camera. To check such a data transmission, the I/F circuit 38 is connected to the camera 66.

Figure 4A:
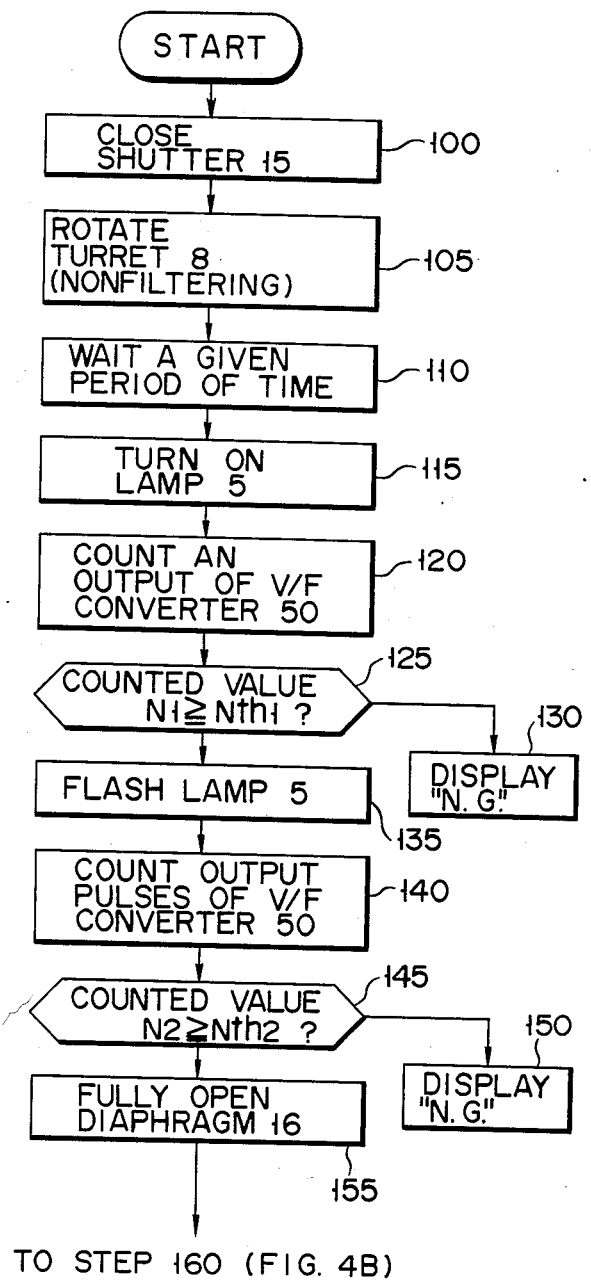

The operation of this embodiment will be given referring to a flowchart on the operation of the CPU 30 shown in FIGS. 4A and 4B. When a check button (not shown) is pushed, the checking operation is started. Upon the start of the operation, the shutter vane 15 is closed to shut off the optical axis L (step 100). The check button is preferably pushed before use of the light source device, but it may be pushed when it is being used. The shutter vane 15 is closed to guide light to the photosensitive element 23 and to prevent the light guide tube 4 from being burnt by the light incident thereon. To increase the amount of light to the photosensitive element 23, the turret 8 is turned so that an empty filter (a mere through hole) lies on the optical axis L (step 105). Allowing for a mechanical delay in the turn of the turret 8, the CPU 30 executes a wait processing of a given period of time, e.g., 3 seconds (step 110). Subsequently, the lamp 5 is lit to emit a given amount of light (step 115). This lighting of the lamp 5 is merely for checking if the lamp is operating normally. Hence, it is sufficient that the amount of the emitted light is small. The light emitted from the lamp 5 is reflected by the reflecting surface 21 of the shutter vane 15, and applied to the photosensitive element 23. The photosensitive element 23 produces an electrical signal corresponding to the amount of light received. Then, the V/F converter 50 produces a signal (pulse signal) with a frequency corresponding to that light amount. Then, the AND gate 52 is enabled for a given period of time by a gate signal with a fixed duration derived from the I/F circuit 38. The output pulse signal of the V/F converter 50 is inputted to the counter 54 for a fixed period of time. The counter 54 counts the pulse signal from the V/F converter 50 during this period (step 120). In other words, the counter 54 detects the amount of light emitted by the lamp 5 in terms of the number of pulses N1. The detected value N1 is compared with a reference value Nth1 (theoretical value of an amount of light as given when the lamp is lit emitting a predetermined amount of light) (step 125). Through the comparison, it is checked if the lamp operates normally and if the shutter vane 15 is closed correctly. If the detected value N1 is below the reference value Nth1 (NO), either the lighting of the lamp or the closing of the shutter vane 15 is abnormal. The "N.G." is displayed on the display section of the front panel (not shown) (step 130).

When the detected value N1 is above the reference value Nth1 (YES), it is decided that these two states are normal. The CPU 30 starts the next check, viz., the check of flashing of the lamp. The lamp 5 flashes (emits a large amount of light) for photographing an object (step 135). For flashing the lamp 5, the current to the lamp 5 may be increased or a lamp giving the flashing may be selected. As in the case of checking the lighting of the lamp, the number of pulses outputted from the V/F converter 50 during a predetermined period of time is counted by the counter 54 (step 140). A count N2 counted by the counter 54 is compared with a reference value Nth2 (theoretical value of an amount of light emitted when the lamp flashes, which is larger than Nth1) (step 145). When the detected value N2 is below the reference value Nth2 (NO), the flashing of the lamp 5 is abnormal. The "N.G." is displayed on the display section (step 150). If the detected value N2 is above the reference value Nth2, the flashing is normal.

In this embodiment, the amount of emitted light is controlled according to a rotational angle of the diaphragm vane 16. Therefore, the operation of the diaphragm vane 16 is checked. In actual light source devices, variation is unavoidable on the optical axis L and the amount of light from the lamp. For an equal rotational angle of the diaphragm vane 16, the light source devices may have different amounts of light applied to the light guides, respectively, because such variation is present. To check the operation of the diaphragm vane 16, the diaphragm is set at the maximum (fully opened) (step 155).

The frequency of the signal oscillated by the variable frequency oscillator 56 is converted into a voltage by the F/V converter 58. The converted voltage is used as a drive voltage signal for the motor 18. The amount of rotation of the motor 18 is negatively fed back to the mixer 60 through the potentiometer 64. In the mixer 60, the fed back signal is added to the drive voltage signal for the motor 18. As a result, the diaphragm vane 16 stops turning at a position determined by the oscillating frequency of the frequency oscillator 56. An amount of light received by the photosensitive element 23 is obtained, by the counter 54, in terms of the number of pulses n1 produced by the V/F converter 50 during a predetermined period of time (step 160). The diaphragm value (rotational angle of the diaphragm vane) is made to correspond to the amount of light received n1 (counted value) of the photosensitive element 23. These corresponding values are stored as a diaphragm table (step 165). This storing operation is executed for all of the diaphragm values up to the minimum diaphragm value (steps 170 and 175). When the amount of received light ni of the photo-sensitive element 23 at the minimum diaphragm value is obtained, it is checked whether or not the amount of received light of the photosensitive element 23 decreases as the diaphragm is increasingly closed (step 180). If the check result is NO, it is decided that the turning operation of the diaphragm vane 16 is abnormal, and "N.G." is displayed on the front panel (step 185). If the check result is YES, it is decided that the turning operation of the diaphragm vane 16 is normal.

Then, to check the send/reception of data to and from the camera 66, the CPU 30 issues a data send request command to the camera 66 (step 190). It is checked whether or not the camera 66 responds to the data send request command to send data (step 195). If any data is not received from the camera 66, the "N.G." is displayed (step 200).

When the data is received from the camera, it is considered that all of the functions of the light source device are normal. Then, the light source device is ready for the normal operation. To be more specific, the turret 8 is turned so that a given filter is positioned on the optical axis L of the light source light 5 (step 205). The CPU 30 executes the delay time processing to cope with a drive delay of the turret 8 (step 210). Following this step, the shutter vane 16 is opened (the optical axis L is released from its interrupt) (step 215). When, all of the check results are displayed good (step 220).

In the above-mentioned embodiment, five items are checked: lighting of the lamp, flashing of the lamp, operation of the shutter vane, operation of the diaphragm vane and data transfer between the control circuit and the camera. Practically, it is sufficient that at least two items, not all of the items, are checked. The check operation may automatically be started after the power source of the light source device is turned on or connection of the endoscope body to the light source device is checked. As a matter of course, the items to be checked are not limited to the above ones.

As seen from the foregoing description, according to the present invention, the functions of the light source device can be checked by merely pushing a button before the endoscope is used. Further, the check results are visually displayed. Accordingly, an operator can always successfully diagnose patients using the endoscope with normal light source devices, eliminating that restart of diagnosis due to use of a troubled light source device.

What is claimed is:

1. A light source device for an endoscope, comprising: light source means for supplying an amount-adjusted light to an endoscope, having a housing and a light-amount adjusting means; means, provided in said housing, for detecting light, means, provided in said housing, for leading the amount-adjusted light to said light-detecting means, in response to a check start signal; and check means for checking whether or not said light-amount adjusting means is operating normally, based the output of said light-detecting means in each of adjust values obtained sequentially by adjusting the amount of light by said light-amount adjusting means.

2. The light source device according to claim 1, in which said light amount adjusting means has at least two adjusting functions, and said check means successively operates said adjusting functions to continuously check each of said adjusting functions in response to the check start signal.

3. The light source device according to claim 1, in which said check means includes a mode select section for selecting either of said modes of said light emission control section, and a detecting section for detecting the amount of light emitted from said light emitting section, thereby the operation of said light emission control section is checked according to the mode selected by said light emission control section and a detected value by said detecting section.

4. The light source device according to claim 2, in which said check means includes a diaphragm control section, a detecting section for detecting the amount of light illuminated by said light emitting section through a diaphragm, and a memory section for storing a control signal to said diaphragm control section and a detected value by said detecting section, said control signal being made to correspond to said detected signal, thereby the operation of said diaphragm control section is checked according to the relationship between said control signal and said detected value stored in said memory section.

5. The light source device according to claim 2, in which said check means includes a shutter control section, and a detecting section for detecting the amount of light illuminated by said light emitting section through said shutter, thereby the operation of said shutter control section is checked according to a control signal to said shutter control section and the detected value of said detecting section.

6. The light source device according to claim 1, further comprising means for generating a check start signal in response to power on of said light source.

7. The light source device according to claim 1, further comprising means for generating a check start signal in response to connection of an endoscope body to said light source device.

8. The light source device according to claim 1, in which said check signal is generated except when said light source device is in a regular operation.

9. The light source device according to claim 1, further comprising means for displaying the check results by said check means.

10. The light source device according to claim 1, in which said light source includes a light emitting section, a light emission control section to set said light emitting section in a flash mode in which said light emitting section flashes, or in a normal mode in which said light emitting section emits less light than in said flashing mode, a shutter for interrupting the light path between the light emitting section and the endoscope, and for leading the reflected light to said light-detecting means in response to the check start signal and a diaphragm for adjusting the amount of light emitted from said light emitting section.

11. A method for checking a light source device for an endoscope, comprising the steps of: supplying a check start signal to the light source device; turning a shutter means to lead the light from said light source device to a light-detecting means; energizing a light-amount adjusting means to adjust the amount of light; detecting the amount of light led to said light-detecting means; and checking whether or not said light-amount adjusting means is operating normally, based on the output of said light-detecting means.

12. A light source device for an endoscope, comprising:

light source means for supplying a light to an endoscope, having a housing, a light-emitting means, and a light-amount adjusting means for adjusting the amount of the light supplied to the endoscope, said light-amount adjusting means comprising at least one of flashing means for flashing the light-emitting means, diaphragm means for adjusting the amount of the light emitted from the light-emitting means and supplied to the endoscope, and shutter means for selectively preventing the light emitted from the light-emitting means from being supplied to the endoscope, the shutter means having a mirror for reflecting the light emitted from the light-emitting means when said shutter means interrupts the light;

means, provided in said housing, for detecting the light reflected by the mirror; and check means, provided in said housing, for activating said light-emitting means and said shutter means in order to check whether or not said light-emitting means and said shutter means are operating normally, based on the output of said light-detecting means, for activating said flashing means and said shutter means in order to check whether or not said flashing means is operating normally, based on the output of said-light detecting means, and for activating said diaphragm means and said shutter means in order to check whether or not said diaphragm means is operating normally, based on the output of said light-detecting means.

* * * * *